(12) United States Patent
Lee et al.

(10) Patent No.: US 9,938,581 B2
(45) Date of Patent: Apr. 10, 2018

(54) PRIMERS FOR DIAGNOSING AVELLINO CORNEAL DYSTROPHY

(71) Applicant: Avellino Co., Ltd., Gangnam-gu (KR)

(72) Inventors: Gene Lee, Gyeonggi-do (KR); Jung Kuk Yun, Chungcheongbuk-do (KR)

(73) Assignee: Avellino Co., Ltd., Seoul (KR)

( * ) Notice: Subject to any disclaimer, the term of this patent is extended or adjusted under 35 U.S.C. 154(b) by 19 days.

(21) Appl. No.: 14/454,669

(22) Filed: Aug. 7, 2014

(65) Prior Publication Data

US 2015/0093751 A1    Apr. 2, 2015

Related U.S. Application Data

(63) Continuation of application No. 13/264,784, filed as application No. PCT/KR2009/007099 on Dec. 1, 2009.

(30) Foreign Application Priority Data

Apr. 17, 2009    (KR) ........................ 10-2009-0033528

(51) Int. Cl.
    *C12Q 1/68*    (2006.01)
    *C12P 19/34*   (2006.01)

(52) U.S. Cl.
    CPC .......... *C12Q 1/6883* (2013.01); *C12Q 1/686* (2013.01); *C12Q 2600/112* (2013.01); *C12Q 2600/156* (2013.01)

(58) Field of Classification Search
    None
    See application file for complete search history.

(56) References Cited

U.S. PATENT DOCUMENTS

| | | | |
|---|---|---|---|
| 6,018,713 | A | 1/2000 | Coli et al. |
| 6,171,112 | B1 | 1/2001 | Clark et al. |
| 6,331,276 | B1 | 12/2001 | Takei et al. |
| 2003/0176650 | A1 | 9/2003 | Grosse et al. |
| 2003/0204418 | A1 | 10/2003 | Ledley |
| 2003/0211500 | A1 | 11/2003 | Woosley |
| 2004/0217345 | A1 | 11/2004 | Boland et al. |
| 2004/0263853 | A1 | 12/2004 | Hill et al. |
| 2005/0019757 | A1 | 1/2005 | Stolarchuk |
| 2006/0038990 | A1 | 2/2006 | Habib et al. |
| 2006/0057604 | A1 | 3/2006 | Chen et al. |
| 2006/0066249 | A1 | 3/2006 | Wark et al. |
| 2007/0254296 | A1 | 11/2007 | Jiang et al. |
| 2007/0274895 | A1 | 11/2007 | Jesih et al. |
| 2008/0113344 | A1 | 5/2008 | Wirtz et al. |
| 2008/0174775 | A1 | 7/2008 | Moskovits et al. |
| 2008/0267946 | A1 | 10/2008 | Kim et al. |
| 2009/0073447 | A1 | 3/2009 | Dahint et al. |
| 2009/0305394 | A1 | 12/2009 | Lee et al. |
| 2010/0190158 | A1 | 7/2010 | Peitz et al. |
| 2011/0053794 | A1 | 3/2011 | Zhang |
| 2012/0231537 | A1 | 9/2012 | Templeton et al. |
| 2013/0302811 | A1 | 11/2013 | Lee et al. |

FOREIGN PATENT DOCUMENTS

| | | |
|---|---|---|
| CN | 101144812 A | 3/2008 |
| CN | 101374850 A | 2/2009 |
| EP | 1715326 A1 | 10/2006 |
| EP | 1964606 | 9/2008 |
| EP | 2 019 309 A2 | 1/2009 |
| JP | 2006-250668 A | 9/2006 |
| JP | 2009-045057 A | 3/2009 |
| JP | 2009-523442 A | 6/2009 |
| KR | 10-2007-0076532 A | 7/2007 |
| WO | WO 00/58509 A2 | 10/2000 |
| WO | WO 2005/015198 A1 | 2/2005 |
| WO | WO 2005/040756 A2 | 5/2005 |
| WO | WO 2005/114298 A2 | 12/2005 |
| WO | WO 2007/002567 A2 | 1/2007 |
| WO | WO 2007/083928 A1 | 7/2007 |
| WO | WO 2008/089280 A2 | 7/2008 |
| WO | WO 2012044121 A2 | 4/2012 |
| WO | WO 2015/073978 A2 | 5/2015 |

OTHER PUBLICATIONS

GenBank Accession No. AF035627 [retrieved online: http://www.ncib.nim.nih.gov/nuccore/AF035627.1, retrieval date: Dec. 23, 2014] published date Dec. 1997, Skonier et al.

Grove, D.S., "Quantitative Real-Time Polymerase Chain Reaction for the Core Facility Using TagMan and the PerkinElmer/Applled Biosystems Division 7700 Sequence Detector," Journal of Biomolecular Techniques, 1999, vol. 10, pp. 11-16.

Huerva et al., "Role of BIGH3 R124H mutation in the diagnosis of Avellino corneal dystrophy." European Journal of Ophthamology, May 2008, vol. 18, No. 3, pp. 345-350.

Armelao, L., et al., 'Innovative metal oxide-based substrates for DNA Microarrays', Inorganica Chimica Acta, vol. 361, No. 12-13, pp. 3603-3608 (Apr. 10, 2008).

Kim, Jeong Wan et. al., 'Anesthetic experience for patients with malignant gyperthermia susceptibility determined by molecular genetic test', J Korean Ophthalmol Soc vol. 49, No. 9, 2008, pp. 1431-1436.

Romero, P. et al., 'Anticipation in familial lattice corneal dystrophy type I with R124C mutation in the TGFBI (BIGH3) gene', Molecular Vision vol. 14, May 7, 2008, pp. 829-835.

(Continued)

*Primary Examiner* — Young J Kim

(74) *Attorney, Agent, or Firm* — Morgan, Lewis & Bockius LLP

(57) ABSTRACT

The present invention relates to a real-time PCR primer pair and probe for diagnosing Avellino corneal dystrophy, and more particularly to a real-time PCR primer pair and probe for diagnosing Avellino corneal dystrophy, which can accurately diagnose the presence or absence of a mutation in exon 4 of BIGH3 gene, which is responsible for Avellino corneal dystrophy. The use of the primer pair and probe according to the invention can diagnose Avellino corneal dystrophy in a more rapid and accurate manner than a conventional method that uses a DNA chip or PCR.

6 Claims, 3 Drawing Sheets

(56) References Cited

OTHER PUBLICATIONS

Strum, J.C. et al., 'Tissue expression profiling using real-time PCR', Curr Protoc Pharmacol. Nov. 2002;Chapter 6:Unit 6.9. DOI: 10.1002/0471141755.PH0609S18.
Wittwer C.T. et al., 'Real-time multiplex PCR assays', Methods : A Companion to Methods in Enzymology, Academic Press Inc., New York, NY, US, vol. 25, No. 4, Dec. 1, 2001 (Dec. 1, 2001), pp. 430-442.
Yoo, So Young et al., 'Development of a DNA chip for the diagnosis of the most common corneal dystrophies caused by mutations in the betaigh3 gene', Br J Ophthalmol vol. 91, Jan. 10, 2007, pp. 722-727.
Yoshida, S., et al., 'An analysis of BIGH3 mutations in patients with corneal dystrophies in the Kyushu district of Japan', Jpn J Ophthalmol. Jul.-Aug. 2002;46(4):469-71.
Zheng, Y. B., et al., 'Surface plasmons of metal nanostructure arrays: from nanoengineering to active plasmonics', Journal of the Association for Laboratory Automation, vol. 13, No. 4, pp. 215-226 (Jul. 9, 2008).
Afshari, N., et al., "Survey of Patients with Granular, Lattice, Avellino, and Reis-Bucklers Corneal Dystrophies for Mutations in the BIGH3 and Gelsolin Genes", "Arch Ophthalmol", 2001, pp. 16-22, vol. 119.
Dolmetsch, A., et al., "Combined granular-lattice corneal dystrophy (Avellino) in a patient with no known Italian ancestry","Can. J. Ophthalmol.", 1996, pp. 29-31, vol. 31, No. 1.
Holland, E., et al., "Avellino cornea dystrophy. Clinical manifestations and natural history.", "Ophthalmology", 1992, pp. 1564-1568, vol. 99, No. 10.
Jun, R., et al., "Avellino Corneal Dystrophy After Lasik", Ophthalmology:, 2004, pp. 463-468, vol. 111.
Kennedy, S., et al, "Combined granular lattice dystrophy (Avellino corneal dystrophy)", "Br. J. Ophthalmol.", 1996, pp. 489-490, vol. 80.
Miller, S., Et al., "A Simple Salting Out Procedure for Extracting DNA From Human Nucleated Cells" , "Nucleic Acids Research". 1988, pp. 1215, vol. 16, No. 3.
Stewart, H., Et al., "Heterogeneity in granular corneal dystrophy: Identification of three causative mutations in the TGFBI (BIGH3) gene . . . ", "Hum. Mutat", 1999, pp. 126-132, vol. 14.
Avellino Co. Ltd., Notice of Reasons for Rejection, JP 2014-000571, dated Oct. 6, 2015, 7 pgs.
Avellino Co., Ltd. Decision of Rejection, JP2013-531500, dated Aug. 21, 2015, 11 pgs.
Avellino Lab USA Inc., International Preliminary Report on Patentability, PCT/US2014/029466, dated Jul. 14, 2014, 11 pgs.
Lee, Final Office Action, U.S. Appl. No. 13/876,603, dated Nov. 6, 2015, 14 pgs.
Avellino Co. Ltd., Notification of Grant, CN201180056997.7, dated Jul. 16, 2015, 5 pgs.
Korea Advanced Institute of Science and Technology et al., Invitation Pursuant to Rule 62a(1) EPC, EP10810154.4, dated Sep. 1, 2015, 2 pgs.
Avellino Lab USA Inc., International Search Report and Written-Opinion, PCTUS201465975, dated May 18, 2015, 19 pgs.
Avellino, Examination Report, IN7514-CHENP-2011, dated Oct. 15, 2014, 2 pgs.
Avellino, First Examination Report IN7514-CHENP-2011, dated Aug. 7, 2014, 2 pgs.
Avellino, Notice of Reasons for Rejection, JP2014000571, dated Mar. 6, 2015, 6 pgs.
Avellino_First-Office-Action—JP2012505796_dated Oct. 16, 2013, 3 pgs.
Avellino_Second-Office-Action—JP2012505796_dated Oct. 31, 2014, 7 pgs.
Avellino_Certificate-of-Patent—JP2012505796_dated Jun. 24, 2015, 2 pgs.
Avellino, The First Office Action, CN200980159748.3, dated Aug. 31, 2012, 4 pgs.
Avellino, The Second Office Action, CN200980159748.3, dated Jul. 11, 2013, 5 pgs.
Avellino, The Third Office Action, CN200980159748.3, dated Mar. 24, 2014, 5 pgs.
Avellino, Notification of the Office Rejection, CN200980159748.3, dated Aug. 6, 2014, 4 pgs.
Avellino, Letters Patent, CN200980159748.3, dated Apr. 8, 2015, 2 pgs.
Avelino_Notice-of-Reasons-for-Rejection—JP2013531500_dated Oct. 21, 2014, 5 pgs.
Avellino_the-First-Office-Action—CN201180056997-7_dated Dec. 22, 2014, 4 pgs.
Avellino_International-Search-Rpt-Written-Opinion—PCTUS2014029466_dated Jul. 14, 2014, 11 pgs.
Biotechnology Journal, 2006, vol. 6, No. 5, pp. 621-624.
Chakravarthi et al, TGFBI Gene Mutations Causing Lattice and Granular Corneal Dystrophies in Indian Patients, Investigative Ophthalmology & Visual Science, Jan. 2005, vol. 46, No. 1, 5 pgs.
Database Genbank, Dec. 10, 1997, Database accession No. AF035627, 2 pgs.
Han et al., "Clinical Findings and Treatments of Granular Corneal Dystrophy Type 2 (Avellino Corneal Dystrophy): A Review of the Literature," Eye & Contact Lens, vol. 36, No. 5, Sep. 2010, 4 pgs.
Lee, Office Action, U.S. Appl. No. 13/264,784, dated Sep. 12, 2013, 14 pgs.
Lee, Final Office Action, U.S. Appl. No. 13/264,784, dated May 7, 2014, 26 pgs.
Lee, Final Office Action, U.S. Appl. No. 13/391,167, dated May 18, 2015, 16 pgs.
Lee, Office Action, U.S. Appl. No. 13/391,167, dated Dec. 29, 2014, 9 pgs.
Lee, Office Action, U.S. Appl. No. 13/876,603, dated Apr. 13, 2015, 11 pgs.
NCBI, "*Homo sapiens* Transforming Growth Factor, Beta-Induced, 68kDa (TGFBI), Mrna," NCBI Reference Sequence NM_000358.2, release 107, Mar. 13, 2015, 6 pgs.
Paliwal et al., Heterozygous Change T>G in the Sequence of Exon 12 of TGFBI Gene Seen in a Patienet with Corneal Dystrophy, Genbank :GQ368823.1, National Center for Biotechnology Information, Genbank, Jul. 28, 2009. 6 pgs.
Halfon, P., et al., "Detection of IL28B SNP DNA from Buccal Epithelial Cells, Small Amounts of Serum and Dried Blood Spots," Mar. 2012, Plos ONE, vol. 7, Issue 3, Article No. e33000, pp. 1-6.
Kephart, D., "Rapid Isolation of Genomic DNA from Small Quantities of Human Tissue," 1999, Profiles in DNA, vol. 2, No. 3, pp. 7-9.
Lee, Notice of Allowance, U.S. Appl. No. 13/391,167, dated Jul. 27, 2015, 9 pgs.
Avellino Co. Ltd., Certificate of Patent, JP 2014-000571, dated Apr. 1, 2016, 5 pgs.
Avellino Co. Ltd., Patent Examination Report No. 1, AU2009344501, dated Sep. 24, 2012, 3 pgs.
Avellino Co. Ltd., Patent Examination Rpt-No3-AU2009344501, dated Nov. 25, 2013, 4 pgs.
Avellino Co. Ltd., Decision to Grant, EP09843403.8, dated Feb. 10, 2014, 1 pg.
Avellino Co. Ltd., Patent Certificate, EP09843403-8, dated Oct. 29, 29 2014, 1 pg.
Avellino Co. Ltd., Invitation to Respond to Written Opinion, SG201107572.8, dated Jan. 29, 2014, 12 pgs.
Avellino Co. Ltd., Certificate of Patent, ZA2011/07967, dated Aug. 28, 2013, 1 pg.
Avellino Co. Ltd.,Decision of Grant, RU2011146553, dated Jul. 23, 2014, 2 pgs.
Avellino Co. Ltd., Letters Patent, RU2011146553, dated Dec. 17, 2014, 1 pg.
Avellino Co. Ltd., The First Office Action, CN201080047181.3, dated Jul. 15, 2013, 1 pg.
Avellino Co. Ltd., Certificate of Patent, JP2012525483, dated Jan. 10, 2014, 5 pgs.
Avellino Co. Ltd., First office Action, IL215845, dated Jul. 10, 2013, 4 pgs.

(56) References Cited

OTHER PUBLICATIONS

Avellino Co. Ltd., Further Office Action, IL215845, dated Mar. 25, 2014, 4 pgs.
Avellino Lab, Extended European Search Report, EP14762603.0, dated Jul. 14, 2016, 11 pgs.
Avellino Lab USA Inc., International Preliminary Report on Patentability, PCT/US2014/065975, dated May 17, 2016, 12 pgs.
Korea Advanced Institute of Science and Technology et al., Extended European Search Report, EP10810154.4, dated Jan. 18, 2016, 9 pgs.
Cao W. et al., "Comparison of Methods for DNA Extraction from Paraffin-Embedded Tissues and Buccal Cells," Cancer Detection and Prevention, Elsevier Science, NL, vol. 27, No. 5, Jan. 1, 2003, 8 pgs.
Endo T et al., "Label-Free Detectionof Peptide Nucleic Acid-DNA Hybridization Using Localized Surface Plasmon Resonance Based Optical Biosensor," Analytical Chemisty, American Chemical Society, US, vol. 77, No. 21, 8 pgs. (2005).
Lounsbury Jenny et al., "Enhanced Recovery of Spermatozoa and Comprehensive Lysis of Epithelial Cells from Sexual Assault Samples Having a Low Cell Counts for Aged Up to One Year," Forensic Science International: Genetics, vol. 8, No. 1, Jan. 2014, 6 pgs.
Morbini Patrizia et al., "Oral HPV Infection and Persistence in Patients with Head and Neck Cancer," Oral Surgery, Oral Medicine, Oral Pathology and Oral Radiology, vol. 116, No. 4, Oct. 2013, 11 pgs.
Neuhaus, T., et al., "Reliability of Non-Invasively Acquired Human Genomic DNA as a Substrate for Real-Time PCR-Assisted Analysis of Genetic Polymorphisms," Archives of Toxicology, vol. 78, No. 7, Jul. 1, 2004, 7 pgs.
Avellino Co., Certificate of Patent, JP2013-531500, dated Jan. 13, 2017, 3 pgs.
Avellino Co. Ltd., First Office Action, CN201510121642.1, dated Aug. 12, 2016, 8 pgs.
Avellino Lab, Communication Pursuant to Rules 161(2) and 162, EP14862501, dated Jul. 21, 2016, 2 pgs.
Avellino Lab, Communication Pursuant to Rules 70(2) and 70a(2), EP14762603.0, dated Aug. 2, 2016, 12 pgs.
Beer et al., On-Chip, Real-Time, Single-Copy Polymerase Chain Reaction in Picoliter Droplets, 2007, Analytical Chemistry 79 (22): 8471.
Chao-Shern, Office Action, U.S. Appl. No. 14/788,572, dated Dec. 16, 2016, 14 pgs.
Lee, Office Action, U.S. Appl. No. 13/876,603, dated Nov. 3, 2016, 12 pgs.
Lee, Office Action, U.S. Appl. No. 14/472,325, dated Dec. 19, 2016, 18 pgs.
Richards, et al., Multiplex PCR Amplification from the CFTR Gene Using DNA Prepared from Buccal Brushes/Swabs, 1993, Human Molecular Genetics 2 (2): 159-163.
Walker et al., Collection of Genomic DNA by Buccal Swabs for Polymerase Chain Reaction-Based Biomaker Assays, 1999, Environmental Health Perspectives 107 (7):517.
Avellino Co. Ltd., 2nd Office Action, CN201510121642.1, dated Jun. 28, 2017, 7 pgs.
Avellino Co. Ltd., Office Action, IDW-00201103762, dated Jul. 6, 2017, 3 pgs.
Avellino Lab, Formality Office Action JP2016531678, dated Mar. 29, 2017, 3 pgs.
Korea Advanced Institute of Science and Technology et al., Communication Pursuant Article 94(3), EP10810154.4, dated Nov. 6, 2017, 5 pgs.

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
tccaccacca ctcagctgta                                              20

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
ccatctcagg cctcagctt                                               19

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
tgcagcccta ccactctcaa                                              20

<210> SEQ ID NO 4
<211> LENGTH: 16
<212> TYPE: DNA
<213> ORGANISM: Artificial
<220> FEATURE:
<223> OTHER INFORMATION: primer

<400> SEQUENCE: 4
aggcctcgtt gctagg                                                  16

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
tagtctctta ttctaataga                                              20
```

-continued

```
<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gctgcagact ctgtgtttaa                                                  20

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
ccatccctcc ttctgtcttc tg                                               22

<210> SEQ ID NO 8
<211> LENGTH: 16
<212> TYPE: DNA
<213> ORGANISM: Artificial
<220> FEATURE:
<223> OTHER INFORMATION: primer

<400> SEQUENCE: 8
cgggcccctc catctc                                                      16

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
cagagaaggg agggtgtggt t                                                21

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
gggcgaagat ggtgaagct                                                   19

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
tcctcgtcct ctccacctgt a                                                21

<210> SEQ ID NO 12
<211> LENGTH: 17
<212> TYPE: DNA
<213> ORGANISM: Artificial
<220> FEATURE:
<223> OTHER INFORMATION: primer
```

-continued

```
<400> SEQUENCE: 12
agctggcaag gaggccc                                                    17

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
tttgggcttt cccacatgc                                                  19

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ggcagacgga ggtcatctca                                                 20

<210> SEQ ID NO 15
<211> LENGTH: 18
<212> TYPE: DNA
<213> ORGANISM: Artificial
<220> FEATURE:
<223> OTHER INFORMATION: primer

<400> SEQUENCE: 15
gtagtaccgt gctctctg                                                   18

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
agttccccat aagaatcccc c                                               21

<210> SEQ ID NO 17
<211> LENGTH: 17
<212> TYPE: DNA
<213> ORGANISM: Artificial
<220> FEATURE:
<223> OTHER INFORMATION: primer

<400> SEQUENCE: 17
ggctggaccc ccagagg                                                    17

<210> SEQ ID NO 18
<211> LENGTH: 19
<212> TYPE: DNA
<213> ORGANISM: Artificial
<220> FEATURE:
<223> OTHER INFORMATION: primer

<400> SEQUENCE: 18
acccctcggg gaagtaagg                                                  19

<210> SEQ ID NO 19
```

```
<211> LENGTH: 21
<212> TYPE: DNA
<213> ORGANISM: Artificial
<220> FEATURE:
<223> OTHER INFORMATION: primer

<400> SEQUENCE: 19
aacctttacg agaccctggg a                                              21

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
gactcccatc catcatgccc                                                20

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
agtcgttgga tccaccacca                                                20

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
gacgtcattt cctactgttt cagg                                           24

<210> SEQ ID NO 23
<211> LENGTH: 18
<212> TYPE: DNA
<213> ORGANISM: Artificial
<220> FEATURE:
<223> OTHER INFORMATION: primer

<400> SEQUENCE: 23 cccccagaa acagcctg                                                   18

<210> SEQ ID NO 24
<211> LENGTH: 25
<212> TYPE: DNA
<213> ORGANISM: Artificial
<220> FEATURE:
<223> OTHER INFORMATION: primer

<400> SEQUENCE: 24
ttctaagggg ttaaggagaa agctt                                          25

<210> SEQ ID NO 25
<211> LENGTH: 15
<212> TYPE: DNA
<213> ORGANISM: Artificial
<220> FEATURE:
<223> OTHER INFORMATION: probe

<400> SEQUENCE: 25
```
cacggaccgc acgga                                                         15

<210> SEQ ID NO 26
<211> LENGTH: 15
<212> TYPE: DNA
<213> ORGANISM: Artificial
<220> FEATURE:
<223> OTHER INFORMATION: probe

<400> SEQUENCE: 26
cacggaccac acgga                                                         15

<210> SEQ ID NO 27
<211> LENGTH: 14
<212> TYPE: DNA
<213> ORGANISM: Artificial
<220> FEATURE:
<223> OTHER INFORMATION: probe

<400> SEQUENCE: 27
acacggaccg cacg                                                          14

<210> SEQ ID NO 28
<211> LENGTH: 14
<212> TYPE: DNA
<213> ORGANISM: Artificial
<220> FEATURE:
<223> OTHER INFORMATION: probe

<400> SEQUENCE: 28
acacggacca cacg                                                          14

<210> SEQ ID NO 29
<211> LENGTH: 13
<212> TYPE: DNA
<213> ORGANISM: Artificial
<220> FEATURE:
<223> OTHER INFORMATION: probe

<400> SEQUENCE: 29
tacacggacc gca                                                           13

<210> SEQ ID NO 30
<211> LENGTH: 13
<212> TYPE: DNA
<213> ORGANISM: Artificial
<220> FEATURE:
<223> OTHER INFORMATION: probe

<400> SEQUENCE: 30
tacacggacc aca                                                           13

<210> SEQ ID NO 31
<211> LENGTH: 18
<212> TYPE: DNA
<213> ORGANISM: Artificial
<220> FEATURE:
<223> OTHER INFORMATION: probe

<400> SEQUENCE: 31
ctgtacacgg accgcacg                                                      18

<210> SEQ ID NO 32
<211> LENGTH: 18
<212> TYPE: DNA

```
<213> ORGANISM: Artificial
<220> FEATURE:
<223> OTHER INFORMATION: probe

<400> SEQUENCE: 32
ctgtacacgg accacacg                                             18

<210> SEQ ID NO 33
<211> LENGTH: 21
<212> TYPE: DNA
<213> ORGANISM: Artificial
<220> FEATURE:
<223> OTHER INFORMATION: probe

<400> SEQUENCE: 33
ctgtacacgg accgcacgga g                                         21

<210> SEQ ID NO 34
<211> LENGTH: 21
<212> TYPE: DNA
<213> ORGANISM: Artificial
<220> FEATURE:
<223> OTHER INFORMATION: probe

<400> SEQUENCE: 34
ctgtacacgg accacacgga g                                         21

<210> SEQ ID NO 35
<211> LENGTH: 24
<212> TYPE: DNA
<213> ORGANISM: Artificial
<220> FEATURE:
<223> OTHER INFORMATION: probe

<400> SEQUENCE: 35
gctgtacacg gaccgcacgg agaa                                      24

<210> SEQ ID NO 36
<211> LENGTH: 24
<212> TYPE: DNA
<213> ORGANISM: Artificial
<220> FEATURE:
<223> OTHER INFORMATION: probe

<400> SEQUENCE: 36
gctgtacacg gaccacacgg agaa                                      24

<210> SEQ ID NO 37
<211> LENGTH: 15
<212> TYPE: DNA
<213> ORGANISM: Artificial
<220> FEATURE:
<223> OTHER INFORMATION: probe

<400> SEQUENCE: 37
accgcacgga gaagc                                                15

<210> SEQ ID NO 38
<211> LENGTH: 15
<212> TYPE: DNA
<213> ORGANISM: Artificial
<220> FEATURE:
<223> OTHER INFORMATION: probe

<400> SEQUENCE: 38
accacacgga gaagc                                                15
```

```
<210> SEQ ID NO 39
<211> LENGTH: 21
<212> TYPE: DNA
<213> ORGANISM: Artificial
<220> FEATURE:
<223> OTHER INFORMATION: probe

<400> SEQUENCE: 39
accgcacgga gaagctgagg c                                              21

<210> SEQ ID NO 40
<211> LENGTH: 21
<212> TYPE: DNA
<213> ORGANISM: Artificial
<220> FEATURE:
<223> OTHER INFORMATION: probe

<400> SEQUENCE: 40
accacacgga gaagctgagg c                                              21

<210> SEQ ID NO 41
<211> LENGTH: 24
<212> TYPE: DNA
<213> ORGANISM: Artificial
<220> FEATURE:
<223> OTHER INFORMATION: probe

<400> SEQUENCE: 41
accgcacgga gaagctgagg cctg                                           24

<210> SEQ ID NO 42
<211> LENGTH: 24
<212> TYPE: DNA
<213> ORGANISM: Artificial
<220> FEATURE:
<223> OTHER INFORMATION: probe

<400> SEQUENCE: 42
accacacgga gaagctgagg cctg                                           24
```

PRIMERS FOR DIAGNOSING AVELLINO CORNEAL DYSTROPHY

CROSS-REFERENCE TO RELATED APPLICATIONS

This application is a continuation of a U.S. national phase application Ser. No. 13/264,784, filed Dec. 5, 2011 under the provisions of 35 U.S.C. § 371 of International Patent Application No. PCT/KR09/007099 filed Dec. 1, 2009, which in turn claims priority of Korean Patent Application NO. 10-2009-0033528 filed Apr. 17, 2009. The disclosure of such international patent application and Korean priority patent application are hereby incorporated herein by reference in their respective entireties, for all purposes.

TECHNICAL FIELD

The present invention relates to a real-time PCR primer pair and probe for diagnosing Avellino corneal dystrophy, and more particularly to such a real-time PCR primer pair and probe for diagnosing Avellino corneal dystrophy, which can accurately diagnose the presence or absence of a mutation in exon 4 of BIGH3 gene, which is responsible for Avellino corneal dystrophy.

BACKGROUND ART

Corneal dystrophy is an autosomal dominant hereditary disease, which begins with a blurry symptom in the center of cornea and gradually spreads and thus ends up vision loss as a patient gets older. It includes Avellino corneal dystrophy, Granular corneal dystrophy, lattice type I corneal dystrophy, Reis-bucklers corneal dystrophy, etc., and is caused by mutation of a gene coding (β1G-H3 protein.

Heterozygous patients suffering from Avellino corneal dystrophy appear to have severe loss of vision as getting older and homozygous patients appear to have complete loss of vision since 6 years old. Avellino corneal dystrophy is a newly named disease in 1988, divided from generally called Granular corneal dystrophy because it was found to have discrete symptoms and genetic foundation. Also, it has been known to be the most common corneal dystrophy worldwide, 1/340 to 1/1000 of prevalence rate in Korea (the case of heterozygote) based on genetic analysis indicates that it is a common dystrophy (Holland, E. J. et al., *Ophthalmology*, 99:1564, 1992; Kennedy, S. M. et al., Br. *J. Ophthalmol.*, 80:489, 1996; Dolmetsch, A. M. et al., Can. *J. Ophthalmol.*, 31:29, 1996; Afshari, N. A. et al., *Arch. Ophthalmol.*, 119:16, 2001; Stewart, H. S. *Hum. Mutat.*, 14:126, 1999).

The present inventors has found that if a patient suffering from heterozygous Avellino corneal dystrophy has LASIK surgery, 2 years later, opacity of cornea starts to develop aggressively and eventually results in vision loss (Jun, R. M. et al., *Opthalmology*, 111:463, 2004). Previously, eye surgery has been performed with an expectation that LASIK or Excimer Laser surgery would get rid of vision blurriness of a patient suffering from corneal dystrophy. Also, even in Korea, approximately 3 hundred thousand cases of LASIK surgery have been performed, which leads to the assumption that 300 people lost their vision, based on 1/1000 of minimum estimation of heterozygous patients suffering from Avellino corneal dystrophy. Patients who have undergone LASIK surgery are mainly in their 20's and 30's carrying out productive activities; therefore, their vision loss causes serious troubles in both society and economics.

In addition, after approval of LASIK surgery in year 2000 in USA, African American patients suffering from Avellino corneal dystrophy who underwent LASIK surgery have been found to lose eye sight, which infers that plenty of similar cases might be occurring throughout the world.

Therefore, although accurate diagnosis of Avellino corneal dystrophy is required to prevent the progression of Avellino corneal dystrophy by LASIK surgery, the diagnosis of Avellino corneal dystrophy is just conducted by microscopic observation of corneal opacity and thus often doctors miss latent symptoms of patients to perform LASIK surgery, which results in vision loss. Therefore, rapid and precise diagnosis of corneal dystrophy is desperately in need.

A DNA chip for detecting a mutation in BIGH3 gene, which is responsible for Avellino corneal dystrophy, was developed (Korean Patent Laid-Open Publication No. 10-2007-0076532). However, the diagnosis of Avellino corneal dystrophy using said DNA chip disadvantageously require several steps, including a step of amplifying DNA in a sample, a step of hybridizing the amplified DNA with the DNA chip, a step of washing the hybridized DNA chip, and a step of detecting a positive response.

Accordingly, the present inventors have made extensive efforts to develop a method capable of more efficiently diagnosing Avellino corneal dystrophy, and as a result, have found that, if the diagnosis of Avellino corneal dystrophy is performed using a pair of primers having nucleotide sequences of SEQ ID NO: 1 and SEQ ID NO: 2 and probes having nucleotide sequences of SEQ ID NO: 25 and SEQ ID NO: 26 by a real-time PCR method, Avellino corneal dystrophy can be diagnosed in a more rapid and accurate manner than a conventional method, thereby completing the present invention.

DISCLOSURE OF INVENTION

A main object of the present invention is to provide a primer pair and probe for more efficiently and accurately diagnosing Avellino corneal dystrophy using a real-time PCR method.

To achieve the above object, the present invention provides a real-time PCR primer pair for diagnosing Avellino corneal dystrophy, which is represented by nucleotide sequences selected from the group consisting of SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22, and SEQ ID NOs: 23 and 24.

The present invention also provides a real-time PCR probe for diagnosing Avellino corneal dystrophy, which is represented by a nucleotide sequence selected from the group consisting of SEQ ID NO: 25 to SEQ ID NO: 42.

BRIEF DESCRIPTION OF THE DRAWINGS

In FIG. 1, "A" shows the results of real-time PCR carried out using optimal primers and probes, "B" and "C" show the results of real-time PCR carried out using primers different from those in "A".

BEST MODE FOR CARRYING OUT THE INVENTION

In one aspect, the present invention is directed to a real-time PCR primer pair for diagnosing Avellino corneal dystrophy, which is represented by nucleotide sequences selected from the group consisting of SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22, and SEQ ID NOs: 23 and 24.

Avellino corneal dystrophy is a disease caused by genetic abnormality in which the sequence CGC in exon 4 of BIGH3 gene is mutated to CAC so that arginine at residue of BIGH3 protein is mutated to histidine (R124H).

When a real-time PCR method is carried out using primers of the present invention, Avellino corneal dystrophy can be diagnosed in a more rapid and accurate manner than a conventional method that uses a DNA chip.

In the real-time PCR method, it is very difficult to establish temperature conditions, because experiments using primers and probes should be carried out in the same temperature conditions. Particularly, if only one mutation position like Avellino corneal dystrophy is to be detected, primers and probes should be used in temperature conditions in which they can bind. Also, the probes can bind in a very limited temperature range from 1° C. and 3° C. in a state in which only one nucleotide differs between the probe for detecting a normal gene and the probe for detecting a mutant gene.

Figure 1:
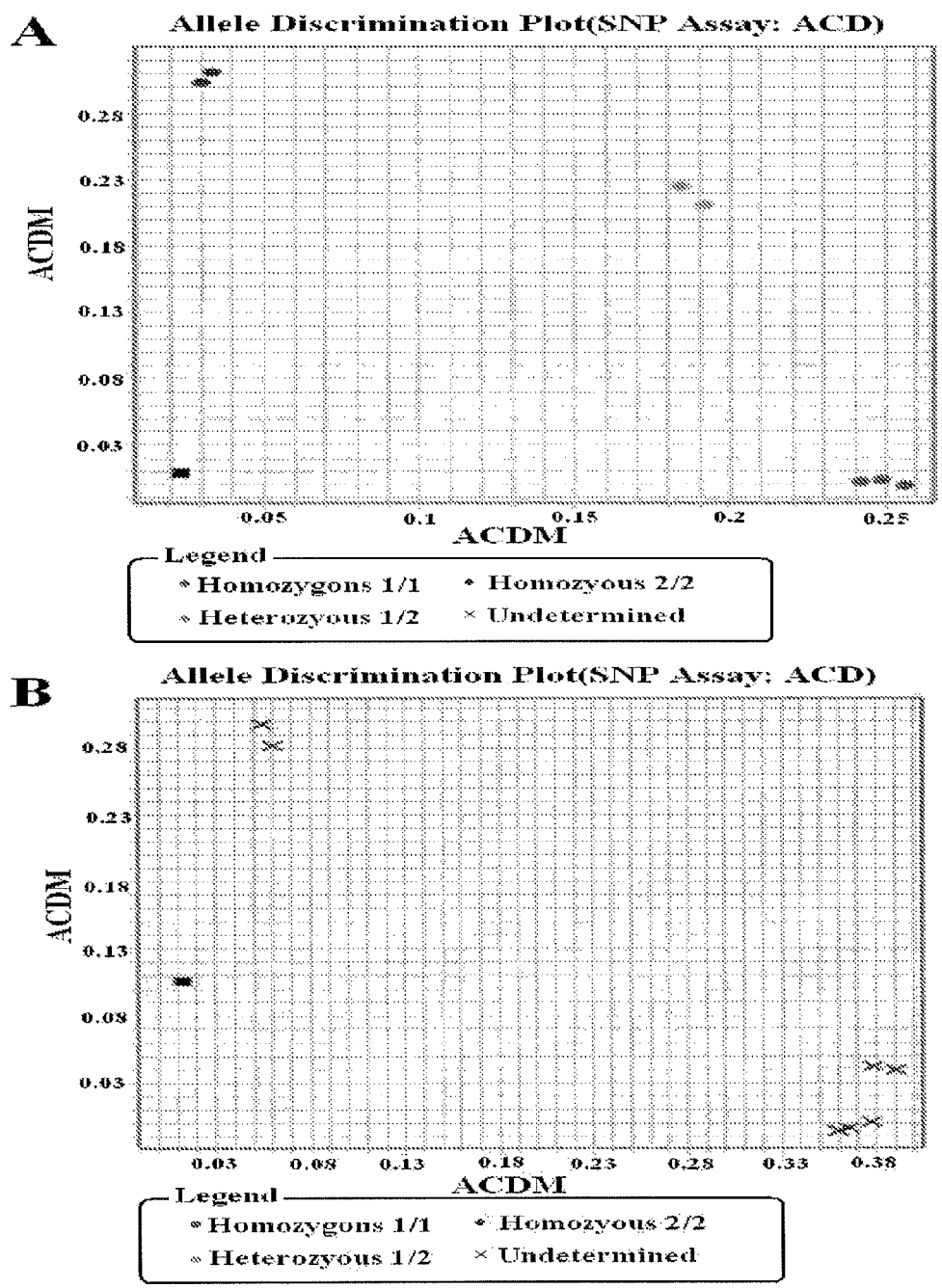
FIG. 1 shows the results obtained from the design of real-time PCR primers and probes.
Figure 1:
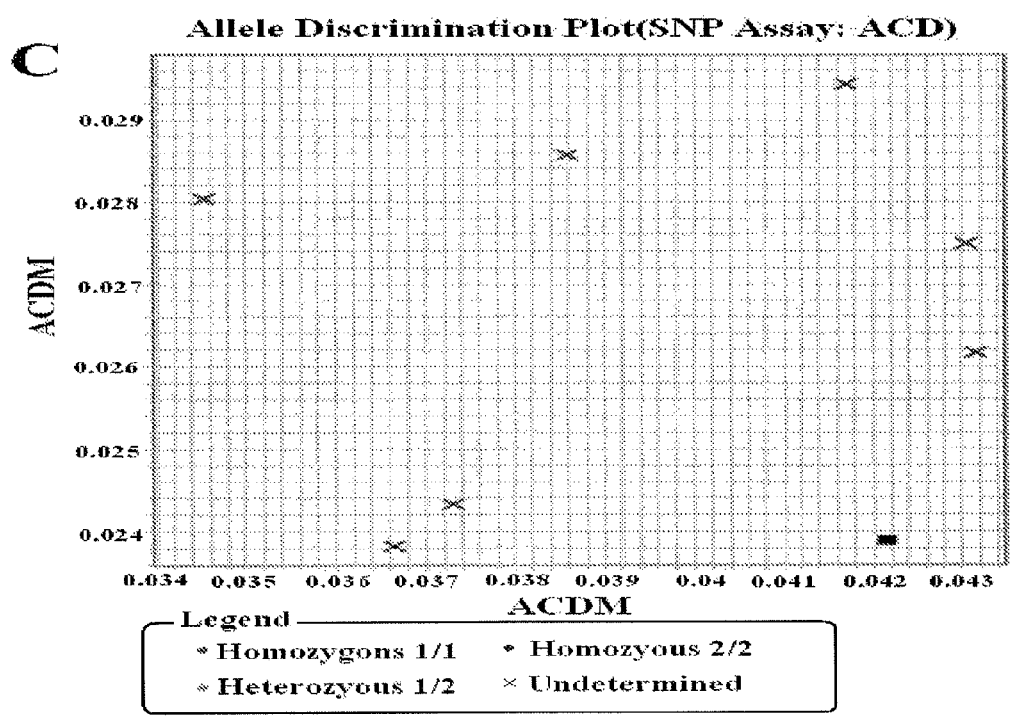

Due to such conditions, it is important to find the same temperature conditions in which probes and primers can bind to a desired gene. Particularly, it is important to design a mutant probe and a normal probe such that the temperatures thereof can differ as much as possible within a limited range. In other words, the temperatures for primers and probes should be well consistent with each other, the temperature conditions for the forward primer and the reverse primer should be well consistent with each other, and the difference between the temperatures for the mutant probe and the normal probe should be able to be maximized. FIG. 1A shows the results of using well-designed primers and probes, and FIGS. 1B and 1C shows the results of using primers different from those used in FIG. 1A while using the same probes as those used in FIG. 1A. As can be seen therein, the design of the primers and the probes has a significant effect on reading.

In the present invention, in order to construct optimal primers for diagnosing Avellino corneal dystrophy using a real-time PCR method, pairs of primers of SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22 and SEQ ID NOs: 23 and 24 were designed, and real-time PCR was performed using each of the designed primer pairs. As a result, it was found that the use of the pair of primers of SEQ ID NOs: 1 and 2 showed the optimal results.

In another aspect, the present invention is directed to a real-time PCR probe for diagnosing Avellino corneal dystrophy, which is represented by a nucleotide sequence selected from the group consisting of SEQ ID NO:25 to SEQ ID NO:42.

In the present invention, in order to construct optimal probes for diagnosing Avellino corneal dystrophy using a real-time PCR method, probes of SEQ ID NOs: 25 to 42 were designed, and real-time PCR was performed each of the designed primers. As a result, it was found that the use of the probes of SEQ ID NOs: 25 and 26 showed the optimal results.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1: Construction of Real-Time PCR Primers and MGB Probes

In order to construct primers capable of amplifying a region comprising a mutation in exon 4 of BIGH3 gene, pairs of primers of SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22 and SEQ ID NOs: 23 and 24 were designed using Primer Express 3.0 software (Applied Biosystems U.S.A).

```
ACD Fw primer:
                                    (SEQ ID NO: 1)
5'-TCC ACC ACC ACT CAG CTG TA ACD Re primer:
                                    (SEQ ID NO: 2)
5'-CCA TCT CAG GCC TCA GCT T (60bp)

AV Fw primer:
                                    (SEQ ID NO: 3)
5'-TGC AGC CCT ACC ACT CTC AA AV Re primer:
                                    (SEQ ID NO: 4)
5'-AGG CCT CGT TGC TAG G (150bp)

Real Fw primer:
                                    (SEQ ID NO: 5)
5'-TAG TCT CTT ATT CTA ATA GA Real Re primer:
                                    (SEQ ID NO: 6)
5'-GCT GCA GAC TCT GTG TTT AA (860bp)

ACD Fw2 primer:
                                    (SEQ ID NO: 7)
5'-CCA TCC CTC CTT CTG TCT TCT G ACD Re2 primer:
                                    (SEQ ID NO: 8)
5'-CGG GCC CCT CCA TCT C (140bp)

ACD Fw3 primer:
                                    (SEQ ID NO: 9)
5'-CAG AGA AGG GAG GGT GTG GTT ACD Re3 primer:
                                    (SEQ ID NO: 10)
5'-GGG CGA AGA TGG TGA AGC T (190bp)

ACD Fw4 primer:
                                    (SEQ ID NO: 11)
5'-TCC TCG TCC TCT CCA CCT GTA
```

```
ACD Re4 primer:
                                        (SEQ ID NO: 12)
5'-AGC TGG CAA GGA GGC CC ACD Fw5 primer:
                                        (SEQ ID NO: 13)
5'-TTT GGG CTT TCC CAC ATG C ACD Re5 primer:
                                        (SEQ ID NO: 14)
5'-GGC AGA CGG AGG TCA TCT CA ACD Fw6 primer:
                                        (SEQ ID NO: 15)
5'-GTA GTA CCG TGC TCT CTG ACD Re6 primer:
                                        (SEQ ID NO: 16)
5'-AGT TCC CCA TAA GAA TCC CCC ACD Fw7 primer:
                                        (SEQ ID NO: 17)
5'-GGC TGG ACC CCC AGA GG ACD Re7 primer:
                                        (SEQ ID NO: 18)
5'-ACC CCT CGG GGA AGT AAG G ACD Fw8 primer:
                                        (SEQ ID NO: 19)
5'-AAC CTT TAC GAG ACC CTG GGA ACD Re8 primer:
                                        (SEQ ID NO: 20)
5'-GAC TCC CAT CCA TCA TGC CC ACD Fw9 primer:
                                        (SEQ ID NO: 21)
5'-AGT CGT TGG ATC CAC CAC CA ACD Reg primer:
                                        (SEQ ID NO: 22)
5'-GAC GTC ATT TCC TAC TGT TTC AGG ACD Fw10 primer:
                                        (SEQ ID NO: 23)
5'-CCC CCC AGA AAC AGC CTG ACD Re10 primer:
                                        (SEQ ID NO: 24)
5'-TTC TAA GGG GTT AAG GAG AAA GCT T
```

In order to detect a guanine-to-adenine mutation in exon 4 of BIGH3 gene, probes of SEQ ID NOs: 25 to 42 were constructed.

The probe binding to a normal gene fragment having no mutation was labeled with VIC, and the probe binding to a gene fragment having a mutation was labeled with FAM, and a minor groove binder (MGB) was attached to the probe so as to facilitate binding to a complementary gene fragment.

```
Normal probe 1:
                                        (SEQ ID NO: 25)
VIC-CAC GGA CCG CAC GGA-NFQ (15bp)

Mutant probe 1:
                                        (SEQ ID NO: 26)
FAM-CAC GGA CCA CAC GGA-NFQ Normal probe 2:
                                        (SEQ ID NO: 27)
VIC-ACA CGG ACC GCA CG-NFQ Mutant probe 2:
                                        (SEQ ID NO: 28)
FAM-ACA CGG ACC ACA CG-NFQ (14bp)

Normal probe 3:
                                        (SEQ ID NO: 29)
VIC-TAC ACG GAC CGC A-NFQ Mutant probe 3:
                                        (SEQ ID NO: 30)
FAM-TAC ACG GAC CAC A-NFQ (13bp)

Normal probe 4:
                                        (SEQ ID NO: 31)
VIC-CTG TAC ACG GAC CGC ACG-NFQ Mutant probe 4:
                                        (SEQ ID NO: 32)
FAM-CTG TAC ACG GAC CAC ACG-NFQ (18bp)

Normal probe 5:
                                        (SEQ ID NO: 33)
VIC-CTG TAC ACG GAC CGC ACG GAG-NFQ Mutant probe 5:
                                        (SEQ ID NO: 34)
FAM-CTG TAC ACG GAC CAC ACG GAG-NFQ (21bp)

Normal probe 6:
                                        (SEQ ID NO: 35)
VIC-GCT GTA CAC GGA CCG CAC GGA GAA-NFQ Mutant probe 6:
                                        (SEQ ID NO: 36)
FAM-GCT GTA CAC GGA CCA CAC GGA GAA-NFQ Normal probe 7:
                                        (SEQ ID NO: 37)
VIC-ACC GCA CGG AGA AGC-NFQ Mutant probe 7:
                                        (SEQ ID NO: 38)
FAM-ACC ACA CGG AGA AGC-NFQ Normal probe 8:
                                        (SEQ ID NO: 39)
VIC-ACC GCA CGG AGA AGC TGA GGC-NFQ Mutant probe 8:
                                        (SEQ ID NO: 40)
FAM-ACC ACA CGG AGA AGC TGA GGC-NFQ Normal probe 8:
                                        (SEQ ID NO: 41)
VIC-ACC GCA CGG AGA AGC TGA GGC CTG-NFQ Mutant probe 8:
                                        (SEQ ID NO: 42)
FAM-ACC ACA CGG AGA AGC TGA GGC CTG-NFQ
```

Example 2: Diagnosis of Avellino Corneal Dystrophy Using Real-Time PCR

Samples were taken from the blood, hair root and oral epithelial cells of test subjects, and DNA was isolated from the samples. The isolation and purification of DNA were performed using a partial modification of the phenol/chloroform extraction method (Miller, S A et al., *Nucl. Acids Res.* 16:1215, 1988), and the isolated DNA was dissolved in a suitable amount of TE buffer (10 mM Tris-Cl, 1 mM EDTA, pH 7.4) and confirmed by electrophoresis on 1% agarose gel and used as template DNA in PCR.

The PCR reactions were performed using the primers (SEQ ID NOs: 1 to 24) for amplifying the fragment containing the mutation region, and the probes (SEQ ID NOs: 25 to 42), constructed in Example 1.

25 μl of a master mix containing 10 pmol of each primer and 5 pmol of each probe was prepared and used in the PCR reaction.

The real-time PCR reaction was performed in the following conditions: 36 cycles each consisting of 10 min at 95° C., 15 sec at 92° C. and 1 min at 60° C., followed by a reaction for 5 min at 60° C.

After each cycle, fluorescence was measured. The sample positive to the VIC dye was diagnosed as having the normal gene, and the sample positive to the FAM gene was diagnosed as having the mutant gene.

Figure 2:
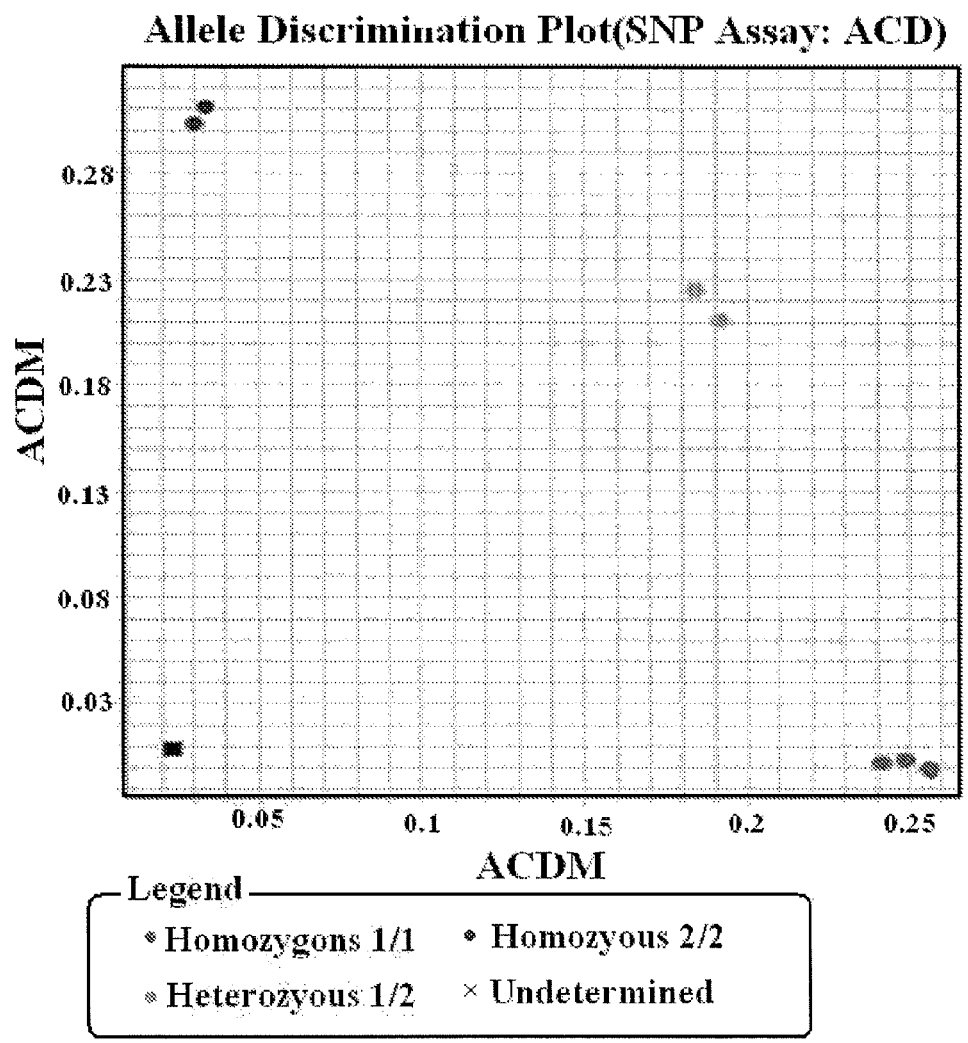
FIG. 2 shows the results of real-time PCR carried out using real-time PCR primers according to the present invention in order to detect a gene mutation causing Avellino corneal dystrophy.

As a result, it could be seen that the use of the primer pair of SEQ ID NOs: 1 and 2 and the probes of SEQ ID NOs: 25 and 26 showed the most accurate and effective results (FIG. 2).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The use of the primer pair and probe according to the present invention can diagnose Avellino corneal dystrophy in a more rapid and accurate manner than a conventional method that uses a DNA chip or PCR.

What is claimed is:

1. A method for detecting Avellino corneal dystrophy comprising:
   (A) performing a real-time polymerase chain reaction (PCR) comprising
      (i) amplifying at least a part of a βIG-H3 gene from a biological sample from a subject using a reaction mixture comprising a first amplification primer and a second amplification primer to produce amplified βIG-H3 nucleotide molecules,
         wherein the first amplification primer is represented by nucleotide sequence SEQ ID NO:1, and
         wherein the second amplification primer is represented by nucleotide sequence SEQ ID NO:2; and
      (ii) hybridizing a detection probe composition to the amplified βIG-H3 nucleotide molecules, wherein the detection probe composition includes a first detection oligonucleotide probe having the nucleotide sequence of SEQ ID NO: 25 and a second detection oligonucleotide probe having the nucleotide sequence of SEQ ID NO: 26, and
   (B) detecting a mutation in the βIG-H3 gene.

2. The method according to claim 1, wherein the first detection oligonucleotide probe is coupled with a first label and the second detection oligonucleotide probe is coupled to a second label, wherein the first label and the second label are different.

3. The method according to claim 2, wherein the first label is VIC and the second label is FAM.

4. The method according to claim 1, further comprising detecting heterozygous Avellino corneal dystrophy in the subject and predicting a risk of complication following a laser eye surgery in the subject.

5. The method according to claim 4, wherein the laser eye surgery comprises Lasik or Excimer laser surgery.

6. The method according to claim 1, wherein the mutation is a R124H βIG-H3 mutation.

* * * * *